US00PP17801P2

(12) United States Plant Patent
Goemans

(10) Patent No.: US PP17,801 P2
(45) Date of Patent: Jun. 12, 2007

(54) ***ALSTROEMERIA* PLANT NAMED 'NATALIE'**

(50) Latin Name: *Alstroemeria hybrida*
Varietal Denomination: Natalie

(75) Inventor: Frank Goemans, Chichester (GB)

(73) Assignee: Wülfinghoff B.V., Rijswijk (NL)

( * ) Notice: Subject to any disclaimer, the term of this patent is extended or adjusted under 35 U.S.C. 154(b) by 0 days.

(21) Appl. No.: 11/311,682

(22) Filed: Dec. 19, 2005

(51) Int. Cl.
*A01H 5/00* (2006.01)

(52) U.S. Cl. ..... Plt./309

(58) Field of Classification Search ..... Plt./309
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Alstroemeria* plant named 'Natalie', characterized by its upright, compact and mounded plant habit; durable and long-lasting leaves; freely flowering habit; large umbels with white and red-colored flowers; and good postproduction longevity.

1 Drawing Sheet

Botanical designation: *Alstroemeria hybrida.*
Cultivar denomination: 'Natalie'.

BACKGROUND OF THE INVENTION

The present Invention relates to a new and distinct cultivar of *Alstroemeria* plant, botanically known as *Alstroemeria hybrida,* commercially used as a potted *Alstroemeria,* and hereinafter referred to by the name 'Natalie'.

The new Alstroemeria is a product of a planned breeding program conducted by the Inventor in Chichester, United Kingdom. The objective of the breeding program was to develop new compact potted *Alstroemeria* cultivars with freely flowering habit, large flowers, attractive flower colors and excellent postproduction longevity.

The new *Alstroemeria* originated from a cross-pollination made by the Inventor in Chichester, United Kingdom, in 1999 a proprietary selection of *Alstroemeria hybrida* identified as code number T 10, not patented, as the female, or seed, parent with a *Alstroemeria hybrida* selection identified as code number 465/l, not patented, as the male, or pollen, parent. The new *Alstroemeria* was discovered and selected by the Inventor as a flowering plant within the progeny of the stated cross-pollination in a controlled environment in Chichester, United Kingdom in 1999.

Asexual reproduction of the new cultivar by tissue culture in a controlled environment in Chichester, United Kingdom, has shown that the unique features of this new *Alstroemeria* are stable and reproduced true to type in successive generations of asexual propagation.

SUMMARY OF THE INVENTION

Plants of the cultivar Natalie have not been observed under all possible environmental conditions. The phenotype may vary somewhat with variations in environment such as temperature and light intensity without, however, any variance in genotype.

The following traits have been repeatedly observed and are determined to be the unique characteristics of 'Natalie'. These characteristics in combination distinguish 'Natalie' as a new and distinct cultivar:

1. Upright, compact and mounded plant habit.
2. Durable and long-lasting leaves.
3. Freely flowering habit.
4. Large umbels with white and red-colored flowers.
5. Good postproduction longevity.

Plants of the new *Alstroemeria* can be compared to plants of the parent selections. Compared to plants of the parent selections, plants of the new *Alstroemeria* flower for a longer period of time and differ in flower color.

Plants of the new *Alstroemeria* can also be compared to plants of the cultivar Sophie, disclosed in U.S. Plant Pat. No. 14,311. In side-by-side comparisons conducted in Sussex, United Kingdom, plants of the new *Alstroemeria* differed from plants of the cultivar Sophie in the following characteristics:

1. Plants of the new *Alstroemeria* were shorter but broader than plants of the cultivar Sophie.
2. Plants of the new *Alstroemeria* were more freely flowering than plants of the cultivar Sophie.
3. Plants of the new *Alstroemeria* flowered for a longer period of time than plants of the cultivar Sophie.

BRIEF DESCRIPTION OF THE PHOTOGRAPHS

The accompanying colored photographs illustrate the overall appearance of the new *Alstroemeria,* showing the colors as true as it is reasonably possible to obtain in colored reproductions of this type. Colors in the photographs may differ slightly from the color values cited in the detailed botanical description which accurately describe the colors of the new *Alstroemeria.*

The photograph at the top of the sheet comprises a side perspective view of a typical plant of 'Natalie' grown in a container.

The photograph at the bottom of the sheet is a close-up view of typical flowers of 'Natalie'.

DETAILED BOTANICAL DESCRIPTION

The aforementioned photographs, following observations and measurements describe plants of the new *Alstroemeria* grown during the summer in 16-cm containers in a glass-covered greenhouse in Sussex, United Kingdom for about six months. During the production of the plants, day temperatures were about 11° C. and night temperatures were about 7° C. Color references are made to The Royal Horticultural Society Colour Chart, 2001 Edition, except where general terms of ordinary dictionary significance are used.

Botanical classification: *Alstroemeria hybrida* cultivar Natalie.

Parentage:

*Female parent.*—*Alstroemeria hybrida* selection identified as code number T 10, not patented.

*Male parent.*—*Alstroemeria hybrida* selection identified as code number 465/1, not patented.

Propagation:

*Type.*—By tissue culture.

*Root description.*—Fibrous, fleshy, thick; white, close to 155D, in color.

*Rooting habit.*—Freely branching.

*Rhizomes.*—Shape: Elongate; rounded. Length: About 5.6 cm. Diameter: About 7 mm. Texture: Smooth. Color: 161A.

Plant description:

*Plant habit.*—Upright, compact and mounded plant habit; freely basal branching, bushy appearance. Moderately vigorous to vigorous growth habit. Leaves sessile.

*Plant height.*—About 16 cm.

*Plant diameter* (*spread*).—About 27 cm.

*Stem description.*—Aspect: Upright to somewhat outwardly spreading. Length: About 16 cm. Internode length: About 2 mm to 2.5 cm. Strength: Strong. Texture: Glabrous, smooth. Color: Between 147C and 146B.

*Foliage description.*—Length: About 5.5 cm to 6 cm. Width: About 1.5 cm to 1.8 cm. Shape: Lanceolate. Apex: Acute. Base: Attenuate. Margin: Entire. Texture, upper and lower surfaces: Smooth, glabrous. Venation pattern: Parallel. Durability: Durable, long-lasting. Color: Developing foliage, upper surface: 145A. Developing foliage, lower surface: 138A. Fully expanded foliage, upper surface: 144B. Fully expanded foliage, lower surface: 138A. Venation, upper surface: 144D. Venation, lower surface: 138A.

Flower description:

*Flower type and habit.*—Single cup-shaped flowers arranged in compound umbels. Flowers face upright to outwardly. Perianth segments separate. Freely flowering habit; about three to twelve flowers per umbel. Flowers not persistent.

*Natural flowering season.*—Plants of the new *Alstroemeria* flower from late spring to autumn in the United Kingdom; flowering continuous during this period.

*Fragrance.*—None detected.

*Flower longevity on the plant.*—About two to three weeks.

*Flower buds.*—Length: About 3.3 cm. Diameter: About 1.7 cm. Shape: Ovoid. Color: 56A; towards the apex, 143B.

*Flower diameter.*—About 6.8 cm.

*Flower height.*—About 4.8 cm.

*Perianth.*—Arrangement: Six arranged in two whorls, each whorl with two lateral and one median segments. Size, inner perianth segments: Length, all segments: About 4.5 cm. Width, all segments: About 1.7 cm. Size, outer perianth segments: Length, all segments: About 4.5 cm. Width, lateral segments: About 2.7 cm. Width, median segment: About 2.5 cm. Shape, inner perianth, all segments: Lanceolate. Shape, outer perianth, all segments: Obovate. Apex, inner perianth, all segments: Acute; mucronate. Apex, outer perianth, all segments: Bracket-shaped; mucronate. Base, inner perianth, all segments: Attenuate. Base, outer perianth, all segments: Cuneate. Margin, inner perianth, all segments: Entire. Margin, outer perianth, all segments: Crenate. Texture, inner and outer perianths, all segments: Smooth, glabrous. Color, inner perianth: When opening and fully opened, all segments, upper surface: Ground color, close to 155D; stripes, close to 53A; towards the base, close to 10B; at base, close to 53D. When opening and fully opened, all segments, lower surface: Close to 155D. Color, outer perianth: When opening and fully opened, all segments, upper surface: Ground color, close to 155D; splotch, close to 53D; at apex, close to 146A. When opening and fully opened, all segments, lower surface: Close to 155D.

*Pedicels.*—Length: About 1.3 cm to 1.9 cm. Diameter: About 1.4 mm to 3 mm. Strength: Strong. Angle: About 15° to 45° from vertical. Texture: Smooth, glabrous. Color: 147B to 147D.

*Reproductive organs.*—Stamens: Quantity per flower: Six. Anther shape: Oval. Anther length: About 0.3 mm to 0.7 mm. Anther color: 164B. Pollen amount: Abundant. Pollen color: 167C. Pistils: Quantity per flower: One. Pistil length: About 3.2 cm. Style length: About 2.9 cm. Style color: 11C. Stigma color: 54A. Ovary color: 141B.

*Fruits.*—Shape: Globular. Length: About 1.4 cm. Diameter: About 9 mm. Color: 141B.

*Seeds.*—Seed development has not been observed.

Disease/pest resistance: Plants of the new *Alstroemeria* have not been observed to be resistant to pathogens and pests common to *Alstroemerias*.

Temperature tolerance: Plants of the new *Alstroemeria* have been observed to tolerate temperatures from 5° C. to 40° C.

It is claimed:

1. A new and distinct cultivar of *Alstroemeria* plant named 'Natalie', as illustrated and described.

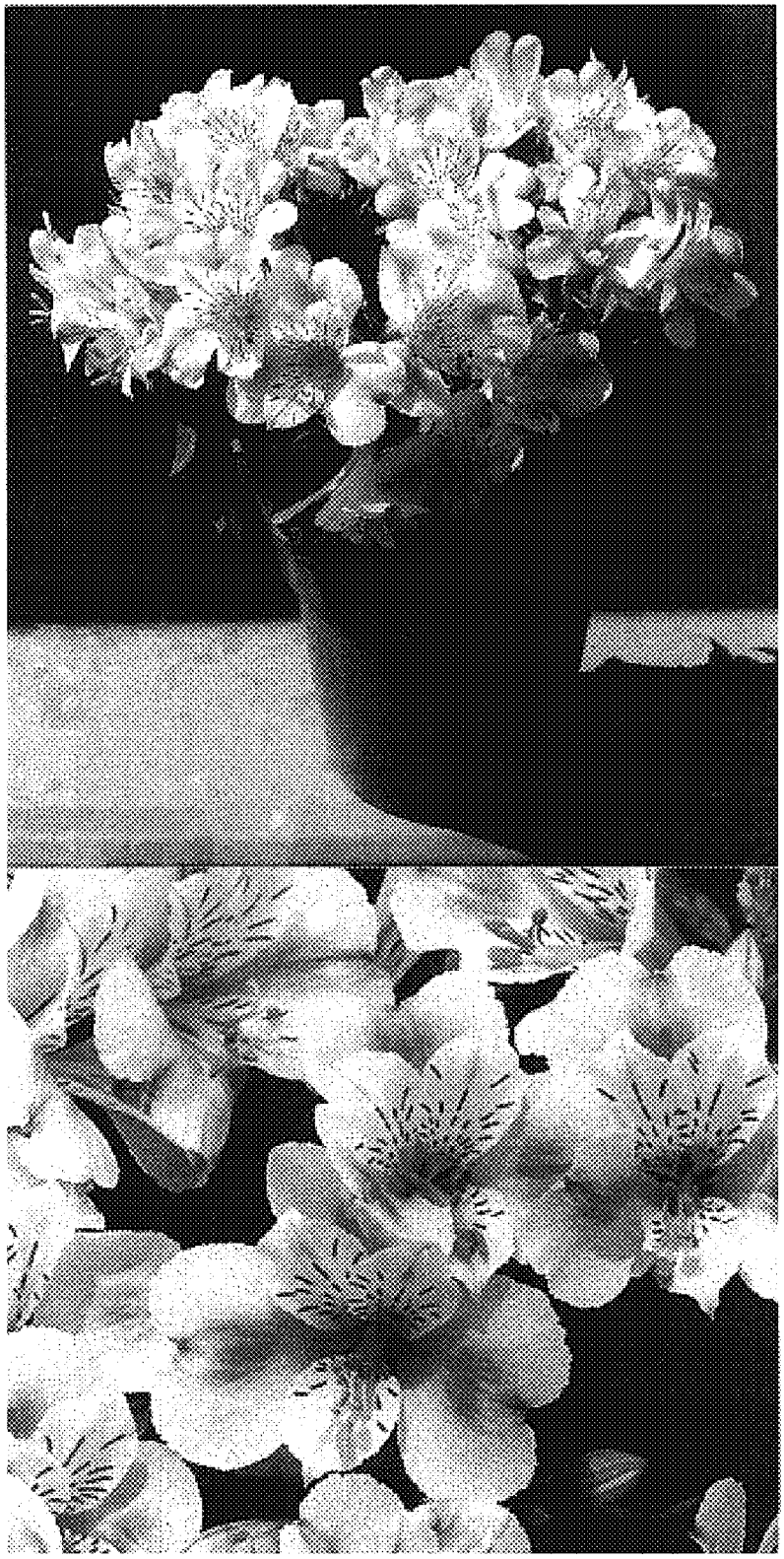

* * * * *